United States Patent
Wikner

(10) Patent No.: US 8,235,952 B2
(45) Date of Patent: Aug. 7, 2012

(54) AUTO INJECTOR

(75) Inventor: Jakob Wikner, Täby (SE)

(73) Assignee: SHL Group AB, Nacka Strand (SE)

(*) Notice: Subject to any disclaimer, the term of this patent is extended or adjusted under 35 U.S.C. 154(b) by 0 days.

(21) Appl. No.: 12/531,335

(22) PCT Filed: Feb. 6, 2008

(86) PCT No.: PCT/EP2008/051441
§ 371 (c)(1),
(2), (4) Date: Sep. 24, 2009

(87) PCT Pub. No.: WO2008/116688
PCT Pub. Date: Oct. 2, 2008

(65) Prior Publication Data
US 2010/0063444 A1 Mar. 11, 2010

(30) Foreign Application Priority Data
Mar. 23, 2007 (SE) ........................... 0700801

(51) Int. Cl.
*A61M 5/32* (2006.01)
*A61M 5/00* (2006.01)
(52) U.S. Cl. ........................ 604/198; 604/187
(58) Field of Classification Search ............... 604/110, 604/192, 198, 68–72
See application file for complete search history.

(56) References Cited

U.S. PATENT DOCUMENTS

| 5,417,660 A * | 5/1995 | Martin ................... 604/110 |
| 6,613,022 B1 * | 9/2003 | Doyle ................... 604/192 |
| 7,357,790 B2 * | 4/2008 | Hommann et al. ........ 604/198 |
| 2008/0077090 A1 * | 3/2008 | Hommann ................ 604/135 |

* cited by examiner

*Primary Examiner* — Jackie Ho
*Assistant Examiner* — Weng Lee
(74) *Attorney, Agent, or Firm* — Potomac Patent Group PLLC

(57) ABSTRACT

The present invention relates to a disposable injection device for delivering a dose of medicament, comprising a generally elongated housing (10), a container (14) containing medicament to be injected through a needle (16), force means (34) acting on said container and capable of, upon activation, move said container and said needle for penetration and subsequently expelling medicament through said needle, activating means (26) arranged to activate said force means, characterized in that said activating means comprises a needle shield (12) arranged slidable in relation to said housing, a collapsible holding member (58) connected to the inner end of said needle shield, whereby, upon movement of said needle shield, said collapsible holding member collapses when a certain force is applied by the needle shield, and whereby further movement of said needle shield activates said activation means, which in turn releases said force means initiating an injection of medicament.

10 Claims, 4 Drawing Sheets

AUTO INJECTOR

This is a national stage application of PCT application NO. PCT/EP08/51441, filed Feb. 6, 2008, which claims priority to Sweden Utility Application No. 0700801-4, filed Mar. 23, 2007, the contents of each of the foregoing are expressly incorporated herein by reference for all purposes.

TECHNICAL FIELD

The present invention relates to an auto-injector comprising needle shield activation of the penetration and subsequent injection.

BACKGROUND ART

For many patients using injecting devices for self-administration of medicament, there is a discomfort to handle the device, especially regarding the penetration. For many users there is a mental resistance against self-penetration. Other users also have a general fear of needles which enhances the discomfort and negative feeling of self-administration. Also, when the needle is about to slowly penetrate human skin; there is a certain start resistance that can give the user discomfort.

It is further desirable for many patients that the number of actions that the patient needs to perform in order to receive a dose of medicament is held as low as possible, on the one hand regarding handling of the device and on the other hand the functionality of the device.

One such device is disclosed in patent EP 1349590 B (SHL MEDICAL AB) 2003-10-08 describing an injector having a number of features that facilitate the handling of the injector. The penetration and injection is performed automatically by pressing a button on the upper end of the injector. When the injection is performed the injector is withdrawn whereby a needle shield extracts around the needle in a locked way. As an additional safety aspect, the activation cannot be performed unless the injector is pressed against an injection site, i.e. a two-step operation to activate the injector is required.

Another type of injecting device is shown in U.S. Pat. No. 5,478,316 (BECTON DICKINSON CO) 1995-12-26 disclosing a high degree of automatic functions. When a sleeve at the front injection end of the injector, being the needle shield, is pressed against an injection site, the sleeve is moved a certain distance into the injector. The movement enables a push button arranged about midway on the side of the injector housing to be pressed by the user. This in turn releases a constant spring means acting on a driver and rod unit in contact with a syringe assembly so that a penetration is performed. When a certain penetration depth is reached, the driver is disconnected from the rod and the rod is urged further by the spring, causing an injection of medicament into the injection site. After the injection is completed the device is withdrawn from the injection site, whereby the sleeve moves forward, covering the needle.

Another aspect of injectors is the human aspect of handling the injector regarding how it is held during operation. A general aim is to have the patient holding the injector in an ergonomic way that may permits the penetration and injection in different locations on the body, such as around the waist and also on the backside of the waist and/or in the buttocks of the patient. The patient does not see the injector at those locations and need to be able to hold the injector without having to change grip. One suitable ergonomic grip for many locations is e.g. the pen grip, whereby the user holds the injector in the front, injection area. This could be difficult when the injector has push buttons on the distal end of the injector or slide buttons on the side of the injector.

DISCLOSURE OF INVENTION

The aim of the present invention is to provide a disposable injection device which addresses the drawbacks of the state of the art.

This aim is obtained by the features of the independent patent claim. Preferable embodiments of the invention form subject of the dependent claims.

According to a main aspect of the invention it is characterised by a disposable injection device for delivering a dose of medicament, comprising a generally elongated housing, a container containing medicament to be injected through a needle, force means acting on said container and capable of, upon activation, move said container and said needle for penetration and subsequently expelling medicament through said needle, activating means arranged to activate said force means, characterised in that said activating means comprises a needle shield arranged slidable in relation to said housing, a collapsible holding member connected to the inner end of said needle shield, whereby, upon movement of said needle shield, said collapsible holding member collapses when a certain force is applied by the needle shield, and whereby further movement of said needle shield activates said activation means, which in turn releases said force means initiating an injection of medicament.

According to another object of the invention, said collapsible holding member comprises at least one elongated member arranged mainly in the longitudinal direction of said injection device.

The at least elongated member could comprise a metal band or a plastic band.

According to a further aspect of the invention, said collapsible holding member comprises a generally tubularly shaped member having a number of longitudinally directed cut-outs, forming a number of elongated strips between the cut-outs.

According to yet an aspect of the invention, said housing is arranged with a space to accommodate parts of the collapsible member when collapsed.

The advantages with the present invention are several. Due to the collapsing holding member, a certain force needs to be applied to the needle shield when pressed against an injection site. The force required means a few advantages. On the one hand, if the injector for some reason hits or is pushed with a rather low force against something, there is a small risk that the needle is exposed in contrast with a needle shield that has no counter force or even a spring urging the needle shield into the extended position, since the force of a spring is lowest when in the uncompressed state. On the other hand, the force required before the collapsible holding means collapses provides a rather fast penetration when collapsing, facilitating the penetration for the patient. The fast penetration also reduces the discomfort of the first penetration of the needle.

Further, due to the rather fast movement during penetration, the subsequent injection will take place rather rapidly. In all a fast and automatic injection process is obtained. The collapsing thus minimizes the risk that the patient will stop the penetration or hesitate, because this is done in a swift movement.

Since the injection device according to the invention preferably is a disposable device, the collapsible holding member is a cost-effective part because it comprises few components that still are capable of performing the desired function. The collapsible member could be made of metal or plastic bands or strips of low cost. Even if it is made as a tubular member, it is cost-effective since the strips then are formed by cutting out longitudinal parts.

Further, the bands or strips have a curved or V-shaped form in cross-section to provide a certain stability or stiffness. It is of course conceivable to have other cross-sectional shapes, such as oval, zig-zag, S-shaped etc. which provide the required stability. The shapes could be modified in order to set different force levels required before the collapsible holding member actually collapses. For example, for persons with weak hands and arms, such as persons having rheumatism, the shapes could be chosen such that a lower force is required.

Regarding persons having difficulties holding the device for injection, such as rheumatics, it is an advantage that the housing is provided with enlargements for accommodating the collapsed holding member, where the enlargement enables a better grip and guide of the injector when using it.

These and other aspects of and advantages with the present invention will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
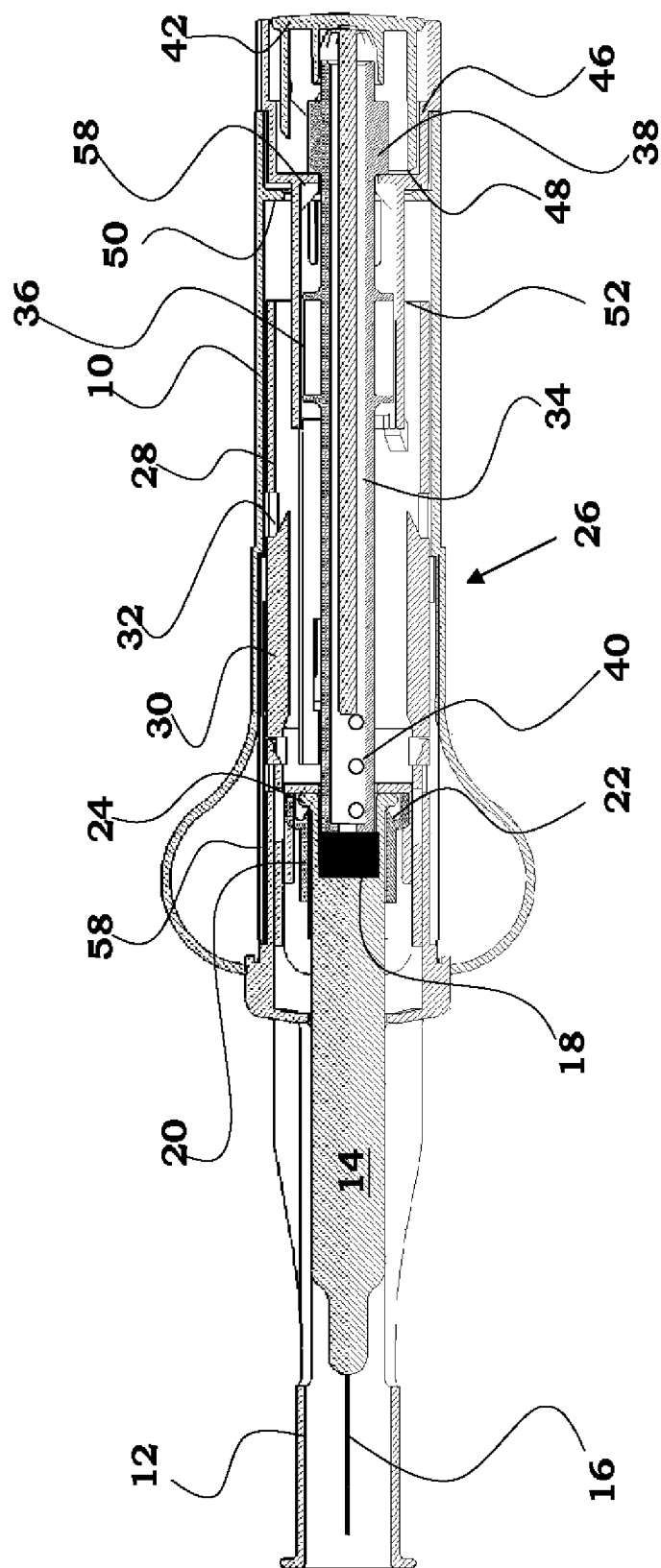
FIG. 1 is a cross-sectional view of an embodiment of an injection device according to the present invention in a locked state before use.
Figure 2:
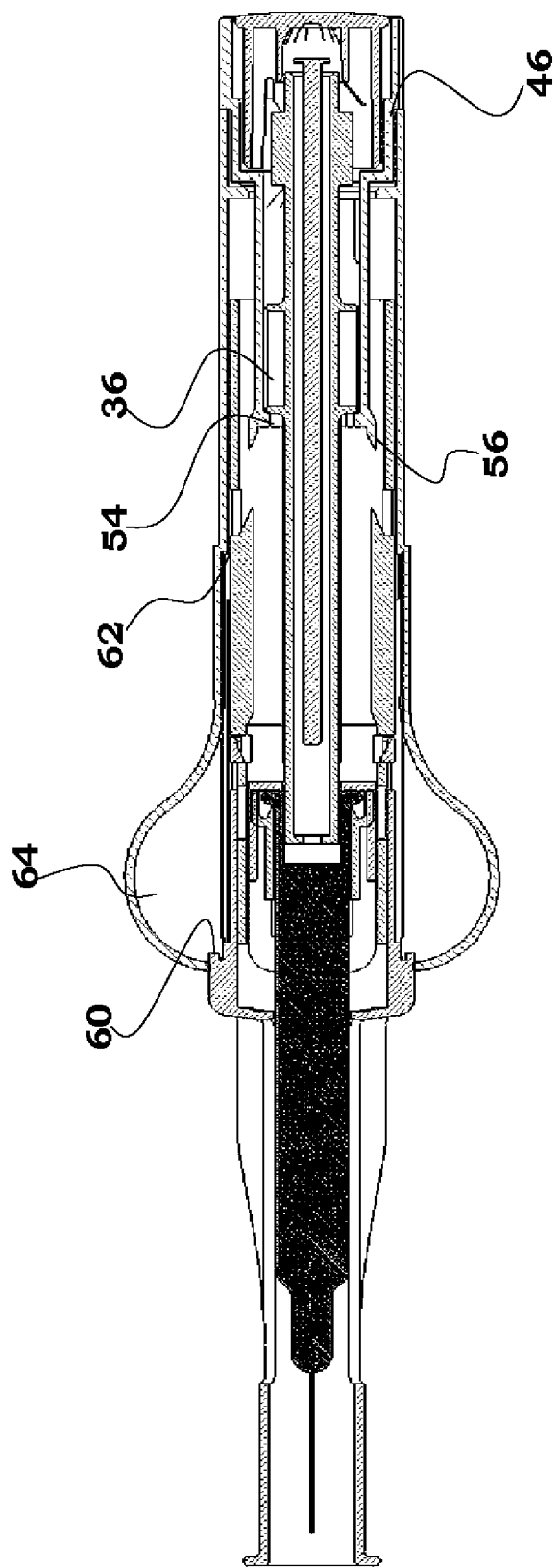
FIG. 2 is a cross-sectional view of the embodiment of FIG. 1 when unlocked and ready for use.
Figure 3:
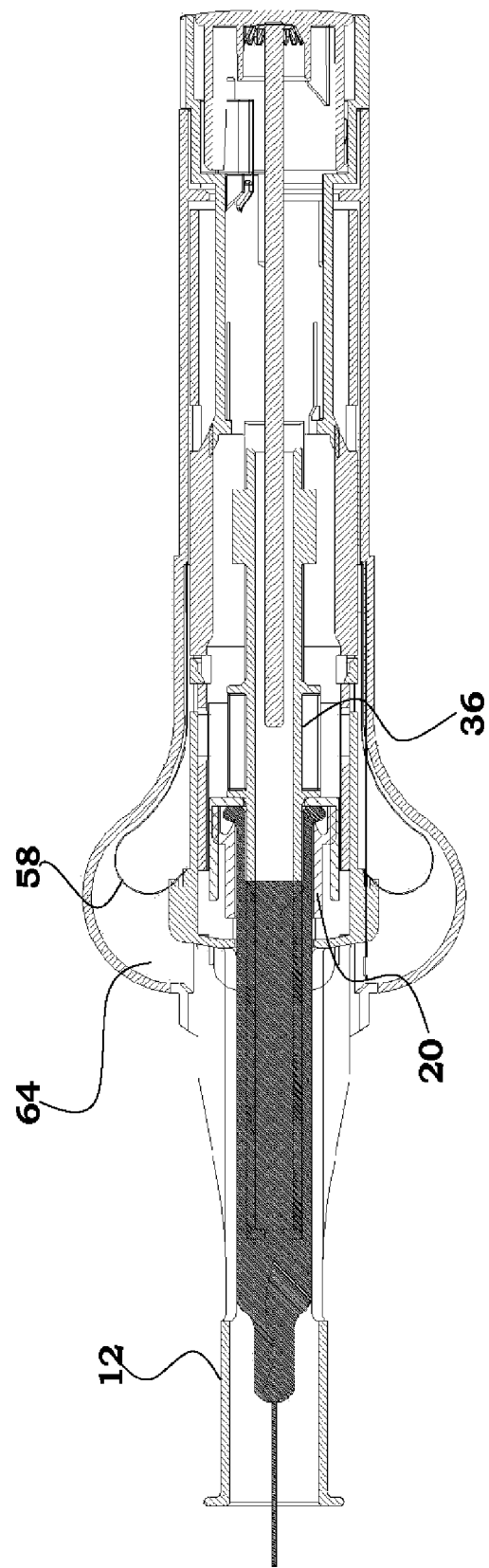
FIG. 3 is a cross-sectional view of the embodiment of FIG. 1 after injection.

An embodiment of an injection device is shown in FIGS. 1, 2 and 3. It comprises a generally tubular elongated housing 10. At the front end of the housing, to the left in the figures, a needle shield 12 is arranged to be slidable in and out of the housing. Inside the needle shield and extending into the housing is a container 14, e.g. a cartridge, a syringe or the like, containing medicament to be injected. A needle 16 is attached to the front end of a cartridge. In the rear end of the container a stopper 18 is arranged. The rear end of the container is inserted into a container holder 20 provided with stop ledges 22 on which a circumferential ledge 24 is resting, for preventing movement of the container. The rear end of the needle shield, to the right in the figures, is in contact with an activating means 26, in the form of a generally tubular elongated member 28 extending into the interior of the housing. The activating means is arranged with inwardly extending longitudinal ledges 30, having a rear edge 32 which is bevelled.

Further a plunger rod 34, comprised in a force means of the injector, is arranged with its front end abutting the stopper 18 of the container. A certain distance along the plunger rod from its front end a first set of two stop ledges 36 are arranged on opposite side of the plunger rod. Further up the plunger rod another set of stop ledges 38 are arranged. The function of the stop ledges will be explained below. Inside the plunger rod, a resilient means 40, e.g. a compression spring, is arranged between an inner front surface of the plunger rod and a rear end wall of an end plug 42 attached to a holding member 46. The holding member is attached to the housing and turnable in relation to the housing and arranged at the rear part of the housing, comprising a first tubular part partly extending at the rear of the housing and having a front surface 48 abutting an inwardly directed circumferential ledge 50 of the housing. The stop member further comprises a second tubular part 52 extending toward the front of the injector. The second tubular part is arranged with longitudinally extending cut-outs, forming arms between the cut-outs. At the front end of the arms, inwardly directed ledges 54, FIG. 2, are arranged. The arms further comprise outwardly directed ledges 56, which ledges are provided with bevelled front edges.

According to the invention a collapsible holding member 58 is arranged between a rearwardly directed ledge 60 of the needle shield and a ledge 62 on the inner surface of the housing. The collapsible holding member comprises two thin bands of a suitable material that is collapsible and preferably is able to return to its original shape when the force is removed. Suitable materials could comprise metal or plastic, where the plastic could be reinforced, etc. The bands are arranged on opposite sides of the needle shield and inserted in grooves in the ledges of the needle shield and housing respectively.

The device according to the invention is intended to function as follows. In FIG. 1 the injector is in locked state. In the locked state, the second set of stop ledges 38 of the plunger rod 34 are resting against inwardly directed ledges 58 of the first part of the holding member 46. A possible protective end cap has been removed from the front end of the needle shield.

When the injector is to be set ready for a dose delivery, the outer, rear part of the holding member is turned, whereby the inwardly directed ledges 58 of the first part of the holding member are moved out of contact with the second set of ledges 38 of the plunger rod 34.

The plunger rod is now free to move forward due to the force of the resilient means 40 until the first set of stop ledges 36 of the plunger rod 34 comes into contact with and are abutting the inwardly directed ledges 54 of the arms, FIG. 2, thereby holding the plunger rod in that position with the resilient means tensioned.

When the patient is to take a dose of medicament he/she presses the front end of the needle shield 12 against the injection site by a certain force. This urges the needle shield to be pressed into the housing of the injector. However, until a certain force level has been reached, the movement of the needle shield is prevented by the thin bands 58 of the collapsible holding member. However when a certain force has been reached, the bands will collapse and bend outwards, which is enabled by a space 64 on each side of the injector arranged in the housing adjacent the bands.

The collapsing of the holding member will enable the needle shield to be pushed further into the housing. Because there is required a certain force until the bands collapse, and the collapsing of the bands occur rather suddenly, the subsequent movement of the needle shield occurs rather suddenly and fast. When the needle shield now moves further suddenly, a fast penetration is obtained.

The further movement of the needle shield and also the sleeve 28 of the activating means, because the inter-contact, will move the inwardly directed bevelled ledges 30, 32 of the activating means to come into contact with the bevelled ledges 56 of the arms of the holding member 46. The bevelled surfaces interact with each other during the movement such that the arms are forced radially outwards. This in turn causes the inwardly directed ledges 54 of the arms to move out of contact with the first set of stop ledges 36 of the plunger rod 34.

The plunger rod is now free to move forward and due to the resilient means 40 acting on the plunger rod, it is urged against the stopper 18 of the container, causes it to move forward, whereby medicament is expelled through the needle 16 and injected into the patient, FIG. 3. The movement of the plunger rod is stopped when the first set of stop ledges 36 abut the container holder 20, or when the stopper 18 reaches the bottom end of the syringe 14.

The injector can now be withdrawn from the injection site whereby the needle shield 12 is pushed forward by the return force of the collapsible holding members now acting as a needle shield resilient means, covering the needle. In this context it is to be understood that a separate needle shield resilient means could be used if the return properties of the collapsible holding member is not sufficient to push the needle shield back to its original position. When in the extended, protective, position, it is locked in place by appropriate locking means, for preventing accidental needle sticks.

Figures 4A, 4B, 4C:
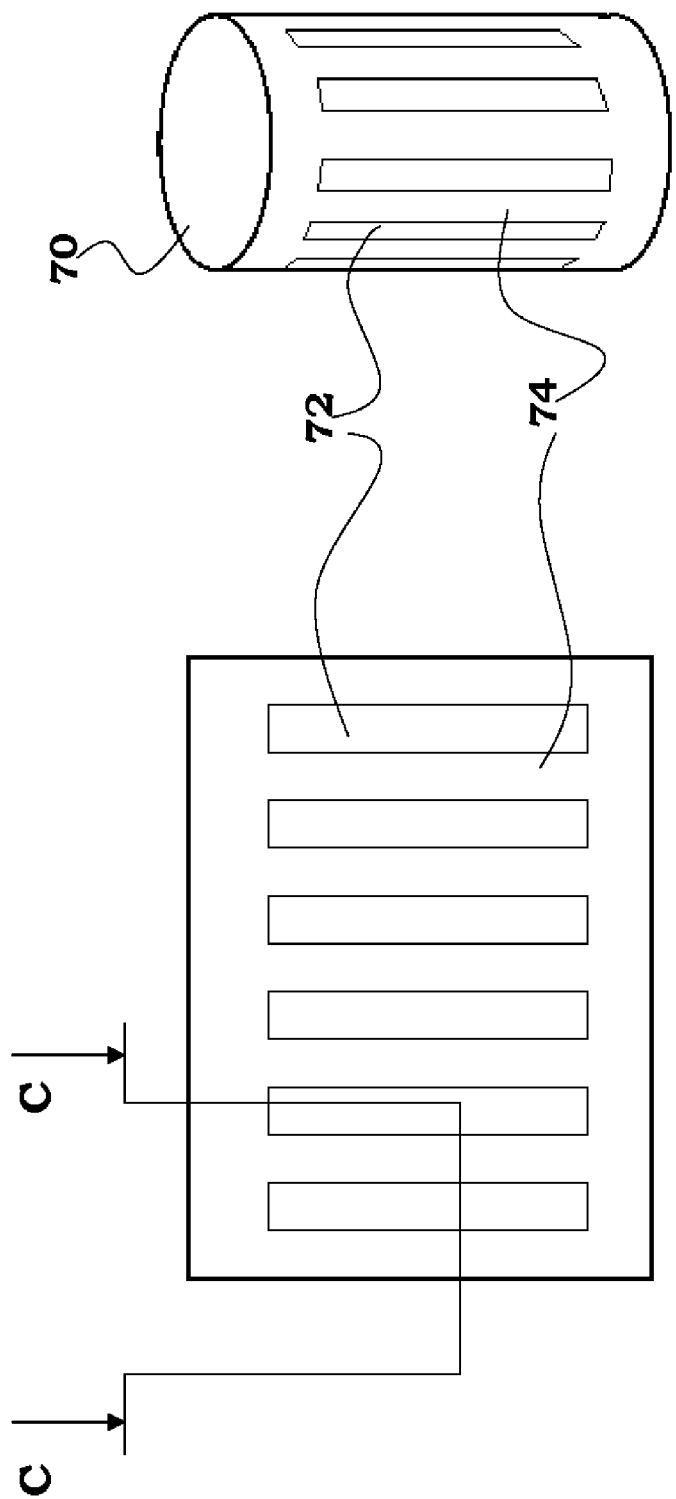
FIG. 4 is another example of a collapsible holding member comprised in the present invention.

It is to be understood that the collapsible holding member can be arranged in many ways and with different choice of materials that fulfil the desired function. For example, as shown in FIG. 4a, the collapsible holding member could be in the form of a tubular member 70 arranged with a number of elongated slits 72, forming a number of elongated strips 74. When the tubular member is compressed, as when the needle shield is pushed into the housing, the strips are bent outwardly, i.e. collapse. The housing is then arranged with an enlargement for accommodating the collapsed strips. Within the scope of the invention, the collapsible holding member also embraces members that resist a certain force, and above that force the resistance is suddenly lowered considerably. Thus, there could also be members that snap or break at a certain force, which provides the same function as when collapsing.

It is further conceivable that the elongated members of the collapsible holding members are arranged such that when a force is applied, a twisting movement is obtained, i.e. the members are twisted when collapsed.

For both embodiments, the enlargement of the housing has an additional advantage in that it enables a very good grip of the injector, which is an advantage for, for example, persons with rheumatism.

Regarding the collapsible holding member, the bands or strips preferably have a somewhat curved or V-shaped form in cross-section, FIG. 4b, which gives them an increased stability and resistibility so that they do not collapse at a too low force. It is of course conceivable to have other cross-sectional shapes, such as oval, zig-zag, S-shaped etc. which provide the required stability. The collapsing force may be modified by choosing different shapes, materials and combinations of these to suit persons with different force capabilities and/or to have different desired functions.

It is to be understood that the embodiments described above and shown in the drawings are to be regarded as only non-limiting examples of the present invention and that it may be modified in many ways within the scope of protection of the patent claims.

In that context it is to be understood that the movement of the needle shield following the collapse of the collapsible holding member could trigger an automatic penetration sequence, i.e. the initial movement of the needle shield does not give a penetration but releases force means that push the whole package with container, needle plunger rod, etc. forwards, to cause an automatic penetration. This could be done by a separate resilient means or with the resilient means of the plunger rod. When the end of the penetration sequence is reached, suitable release means are provided for releasing the plunger rod for injection, alternatively that the force of the plunger rod continues from penetration to injection.

The invention claimed is:

1. A disposable injection device for delivering a dose of medicament, comprising:
   a generally elongated housing;
   a container for containing medicament to be injected through a needle;
   a force device arranged to act on the container; and
   an activating mechanism arranged to activate the force device, and comprising:
      a needle shield slidably arranged in relation to the housing; and
      a collapsible holding member connected to an inner end of the needle shield and arranged between a rearwardly directed ledge of the needle shield and a ledge on an inner surface of the housing;
   whereby upon movement of the needle shield when pressed against an injection site, the collapsible holding member collapses only after at least a certain force applied by the needle shield is reached;
   the needle penetrates and further movement of the needle shield activates the activating mechanism, which in turn releases the force device initiating an injection of medicament;
   the needle shield is pushed forward covering the needle by a return force of the collapsible holding member when the needle shield is removed from the injection site; and
   the needle shield is locked by a locking device arranged to prevent accidental needle sticks.

2. The disposable injection device of claim 1, wherein the collapsible holding member comprises at least one elongated member arranged mainly in a longitudinal direction of the injection device.

3. The disposable injection device of claim 2, wherein the elongated member comprises a metal band.

4. The disposable injection device of claim 2, wherein the elongated member comprises a plastic band.

5. The disposable injection device of claim 2, wherein the elongated member is made of a material that returns to its original shape when the force is removed.

6. The disposable injection device of claim 5, wherein the elongated member comprises a metal band.

7. The disposable injection device of claim 5, wherein the elongated member comprises a plastic band.

8. The disposable injection device of claim 1, wherein the collapsible holding member comprises a generally tubularly shaped member having a number of longitudinally directed cut-outs, forming a number of elongated strips between the cut-outs.

9. The disposable injection device of claim 2, wherein the elongated members have a cross-sectional form that increases stability of the members.

10. The disposable injection device of claim 1, wherein the housing has a space to accommodate a part of the collapsible member when collapsed.

* * * * *